US00PP23168P3

(12) United States Plant Patent
Griffith

(10) Patent No.: US PP23,168 P3
(45) Date of Patent: Nov. 6, 2012

(54) ***LAGERSTROEMIA* PLANT NAMED 'PIILAG-I'**

(50) Latin Name: ***Lagerstroemia* L.**
Varietal Denomination: PIILAG-I

(75) Inventor: Mark P. Griffith, Watkinsville, GA (US)

(73) Assignee: Plant Introductions, Inc., Watkinsville, GA (US)

( * ) Notice: Subject to any disclaimer, the term of this patent is extended or adjusted under 35 U.S.C. 154(b) by 392 days.

(21) Appl. No.: 12/802,193

(22) Filed: Jun. 1, 2010

(65) Prior Publication Data

US 2011/0296571 P1 Dec. 1, 2011

(51) Int. Cl.
*A01H 5/00* (2006.01)

(52) U.S. Cl. ..... Plt./252

(58) Field of Classification Search ..... Plt./252
See application file for complete search history.

(56) References Cited

U.S. PATENT DOCUMENTS

PP17,171 P2 10/2006 Dirr
PP17,411 P2 2/2007 Dirr

OTHER PUBLICATIONS

Plant Introductions, Inc.—page showing color pictures of *Lagerstroemia* selections, (including PIILAG-I) from booklet distributed at trade shows and to nurseries since Jan. 2010.

*Primary Examiner* — Wendy C Haas
(74) *Attorney, Agent, or Firm* — Greenlee Sullivan P.C.

(57) ABSTRACT

A new and distinct cultivar of *Lagerstroemia* plant named 'PIILAG-I', characterized by its dwarf, rounded growth habit that is maintained over time without shoot reversions, reddish new growth and dark green foliage in summer, white flowers, and resistance to powdery mildew and *Cercospora* leaf spot.

4 Drawing Sheets

Genus and species of plant claimed: *Lagerstroemia* L.
Variety denomination: 'PIILAG-I'.

BACKGROUND OF THE INVENTION

The present invention relates to a new and distinct cultivar of *Lagerstroemia* plant, botanically known as *Lagerstroemia* L., commonly known as crapemyrtle, and hereinafter referred to by the cultivar name 'PIILAG-I'.

The new *Lagerstroemia* plant originated from an open-pollination of *Lagerstroemia* 'Gamad V' (U.S. Pat. No. 17,411) in 1999-2000. The cultivar 'PIILAG-I' originated and was discovered in a cultivated environment in Dearing, Ga.

Asexual reproduction of the new cultivar by stem cuttings in Watkinsville, Ga. for three years has shown that all the unique features of this new *Lagerstroemia,* as herein described, are stable and reproduced true-to-type through successive generations of such asexual propagation.

SUMMARY OF THE INVENTION

Plants of the new cultivar 'PIILAG-I' have not been observed under all possible environmental conditions. The phenotype may vary somewhat with changes in light, temperature, soil and rainfall without, however, any variance in genotype.

The following traits have been repeatedly observed and are determined to be unique characteristics of 'PIILAG-I'. These characteristics in combination distinguish 'PIILAG-I' as a new and distinct cultivar: 1. Dwarf, rounded growth habit that is maintained over time without shoot reversions; 2. Reddish new growth and dark green foliage in summer; 3. White flowers; 4. Resistance to powdery mildew and *Cercospora* leaf spot.

Plants of the new *Lagerstroemia* 'PIILAG-I' differ from plants of the parent, 'Gamad V', primarily in flower color and emerging foliage color. Plants of 'Gamad V' have pink flowers and foliage that emerges yellow-green, whereas plants of 'PIILAG-I' have white flowers and foliage that emerges reddish green.

Plants of the new *Lagerstroemia* can be compared to plants of the cultivar 'Gamad III' U.S. Plant Pat. No. 17,171. However, in side-by-side comparisons conducted in Watkinsville, Ga., plants of the new *Lagerstroemia* differed from plants of the cultivar 'Gamad III' in the following characteristics: 1. Plants of the new *Lagerstroemia* were consistently dwarf and did not produce reversion shoots, whereas plants of the cultivar 'Gamad III' would frequently produce reversion shoots and outgrow their original dwarf habit; 2. Plants of the new *Lagerstroemia* produced more inflorescences per plant than similar sized plants of the cultivar 'Gamad III'; 3. Plants of the new *Lagerstroemia* were more vigorous, produced a saleable plant faster, and were more uniform in habit than plants of the cultivar 'Gamad III'; 4. Plants of the new *Lagerstroemia* were more resistant to *Cercospora* leaf spot than plants of the cultivar 'Gamad III'.

BRIEF DESCRIPTION OF THE DRAWINGS

The accompanying color photographs illustrate the flower and foliage characteristics and the overall appearance of the new *Lagerstroemia,* showing the colors as true as it is reasonably possible to obtain in color reproductions of this type. Colors in the photographs may differ slightly from the color values cited in the detailed botanical description which accurately describe the colors of the new *Lagerstroemia.*

DETAILED DESCRIPTION

Figure 1:
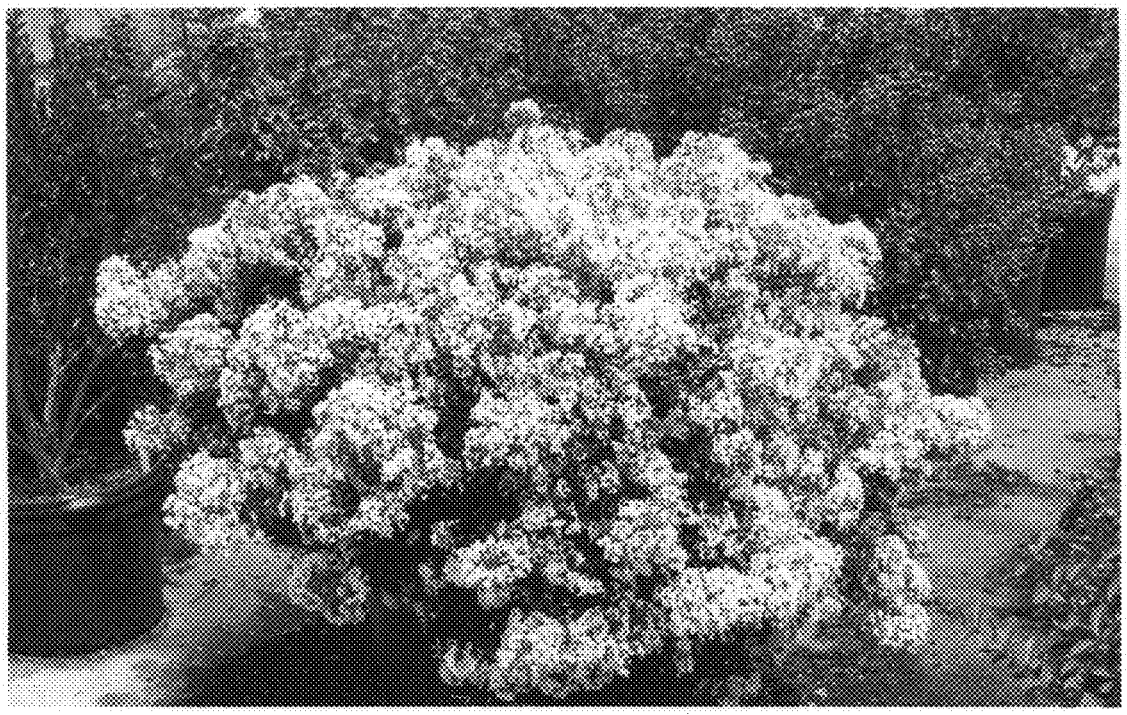
FIG. 1 illustrates the overall appearance of a mature plant of 'PIILAG-I'.
Figure 2:
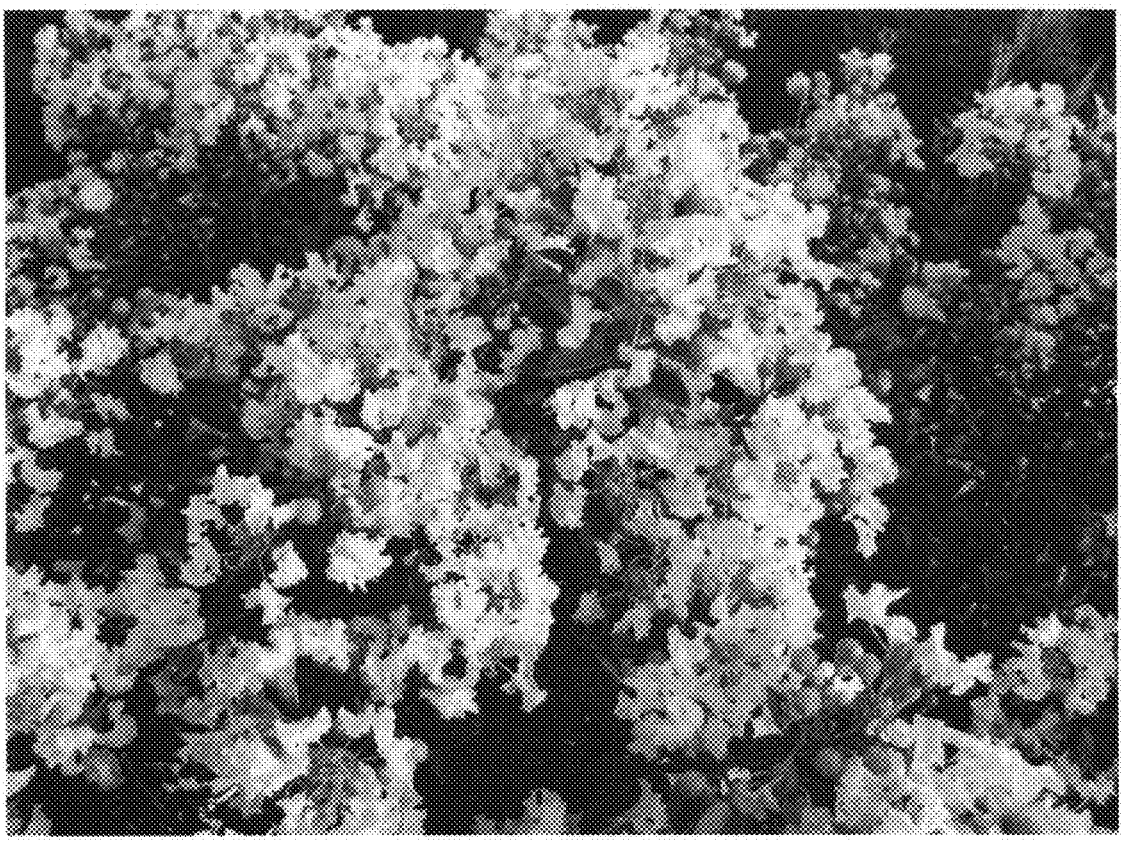
FIG. 2 illustrates a close-up view of the inflorescences of 'PIILAG-I'.
Figure 3:
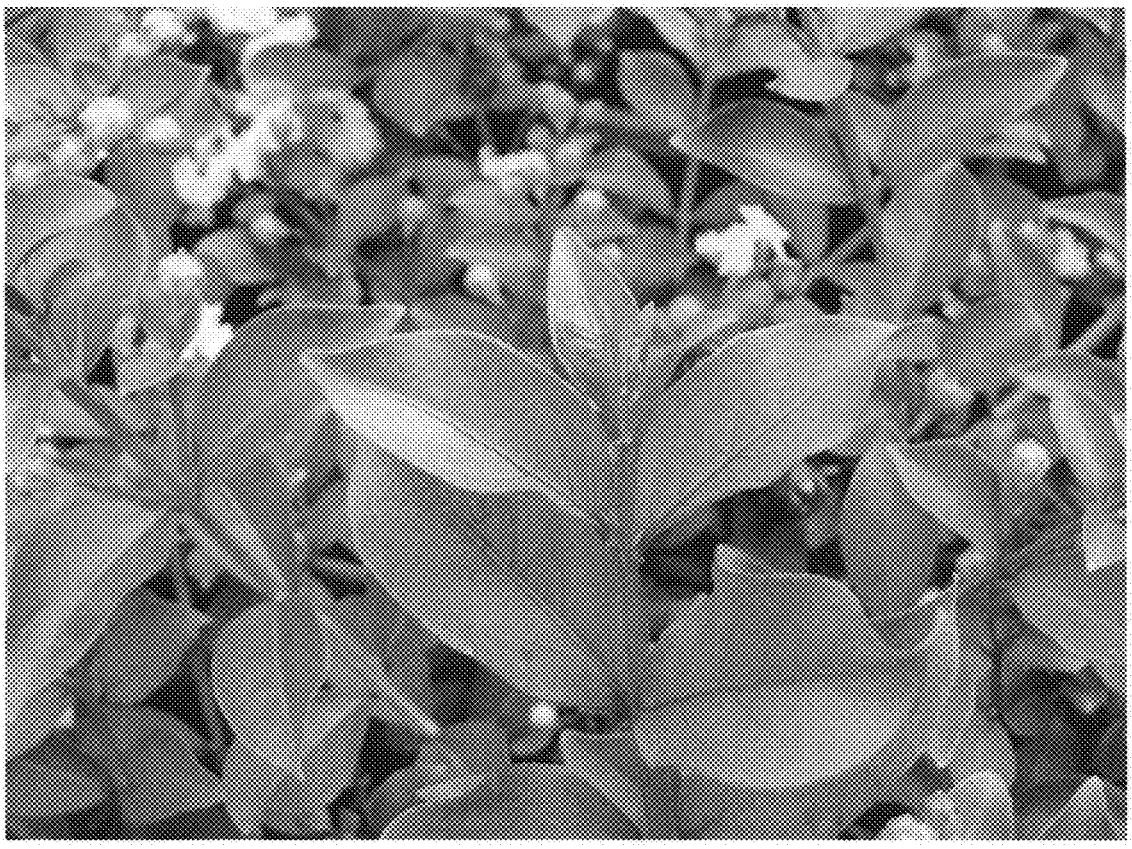
FIG. 3 illustrates a close-up view of the new growth of 'PIILAG-I'.
Figure 4:
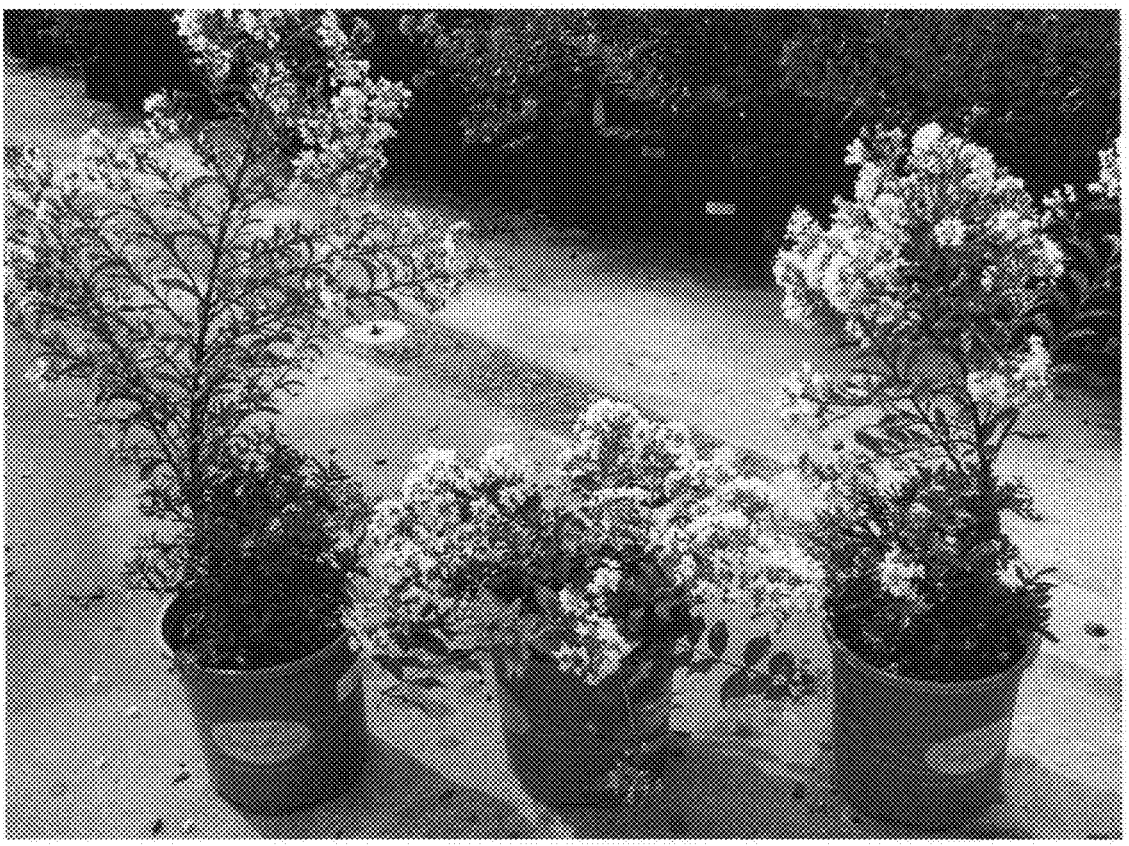
FIG. 4 illustrates a comparison of 'PIILAG-I' (center) to 'Gamad III' with reversions (left and right), respectively.

In the following description, color references are made to The Royal Horticultural Society Colour Chart, 2001 Edition, except where general terms of ordinary dictionary significance are used. Plants used for the description were approximately two and a half years old and were grown in 11.8 L containers under outdoor conditions in Watkinsville, Ga. Colors are described using The Royal Horticultural Society Colour Chart (R.H.S.).

Botanical classification: *Lagerstroemia* L., cultivar 'PIILAG-I'.

Parentage:

*Female, or seed, parent.*—*Lagerstroemia* 'Gamad V'.

*Male, or pollen, parent.*—Unknown (open-pollinated).

Propagation:

*Type cutting.*—Terminal cuttings.

*Time to initiate roots, summer.*—About 21 days at 32° C.

Plant description: Flowering shrub; dwarf, rounded, multi-branched growth habit. Freely branching; pruning enhances lateral branch development.

*Root description.*—Numerous, fine, fibrous and well-branched.

*Plant size.*—The original plant, now about 10 years old, is about 60 cm in height from the soil level to the top of the inflorescences, and about 100 cm in diameter.

*First year stems having a diameter of about* 2 *mm.*—Shape: squarish.

*Second year and older stems have a diameter of about* 4 *mm or more.*—Shape: round.

*Trunk diameter.*—About 1.7 cm at the soil line. Color: close to 199D.

*Internode length.*—About 1.5 cm.

*Strength.*—Flexible when young, easily broken once mature.

*First year stem color* (*young*).—Close to 185A. Color (woody): close to 164A.

*Second year and older stem color.*—Close to 199B.

*Bark.*—Exfoliates in strips beginning on second or third year stems.

Vegetative buds: Sub-opposite to alternate in arrangement, imbricate, conical, with no pubescence.

*Color.*—Close to 175B.

*Size.*—About 3 mm in length and 2 mm in width.

Foliage description:

*Arrangement.*—Sub-opposite to alternate, simple.

*Length.*—About 3.3 cm.

*Width.*—About 1.7 cm.

*Shape.*—Elliptical.

*Apex.*—Acute.

*Base.*—Cuneate.

*Margin.*—Entire.

*Surface.*—Undulating.

*Texture* (*upper surface and lower surfaces*).—Glabrous.

*Venation pattern.*—Pinnate.

*Venation color of emerging foliage* (*upper and lower surfaces*).—Close to 179A.

*Venation color of mature foliage* (*upper surface*).—Close to 144B.

*Venation color of mature foliage* (*lower surface*).—Close to 144D.

*Color in developing foliage* (*upper and lower surface*) .—Close to 179B.

*Color in fully expanded foliage* (*upper surface*).—Close to 137A.

*Color in fully expanded foliage* (*lower surface*).—Close to 146B.

*Color of leaf margin in developing foliage* (*upper and lower surfaces*).—Close to 179A.

*Color of leaf margin in mature foliage* (*upper and lower surfaces*).—Ranges from 179B to 144B.

*Fall color.*—Ranges from 1C to 5C.

*Petiole length.*—About 1 mm.

*Petiole diameter.*—About 1 mm.

*Petiole color.*—Close to 183B.

*Pubescence.*—None.

Flower description: Flowers are produced during July and August in Watkinsville, Ga. An inflorescence is showy for about two weeks, and individual flowers last about one day and are self-cleaning.

*Inflorescence type.*—Panicle.

*Inflorescence length.*—About 10 cm.

*Inflorescence width.*—About 10 cm.

*Peduncle.*—About 8.5 cm in length, about 1.5 mm in diameter, color is close to 144A, and no pubescence.

*Individual flowers.*—About 2 cm by 2.5 cm.

*Flower buds.*—Length: about 6 mm; Diameter: about 6 mm; Color: close to 149C, maturing close to 47A.

*Pedicels.*—About 6 mm in length, close to 144A in color, and no pubescence.

*Calyx.*—About 6 mm in length, about 6 mm in diameter, color close to 144A, and no pubescence.

Petals:

*Arrangement/appearance.*—Usually 6 per flower.

*Petal length.*—About 1.2 cm.

*Petal width.*—About 1 cm.

*Petal shape.*—Fan-shaped.

*Petal apex.*—Ruffled, rounded.

*Petal base.*—Sagittate.

*Petal margin.*—Ruffled.

*Petal texture* (*upper and lower surfaces*).—Glabrous.

*Petal color.*—Upper and lower surfaces are close to N155A.

Stamens:

*Quantity/arrangement.*—About 20 to 25 short stamens clustered in the center, about 7 mm long, filament color is close to 155C, and anther color is close to 16A. The short stamens are surrounded by 6 longer stamens, about 1.3 cm long. Filament color is close to 65B, and anther color is close to 16A. The stamens are not pubescent.

*Pollen.*—Produced in moderate quantities and is close to 145C in color.

Pistils:

*Quantity.*—One superior pistil per flower.

*Pubescence.*—None.

*Pistil length.*—About 2 cm in length.

*Stigma shape.*—Round, about 1 mm in diameter.

*Stigma color.*—Close to 148B.

*Style color.*—Close to 181D and about 1.2 cm in length.

*Ovary color.*—Close to 160A and about 2 mm in diameter.

Fruit:

*Type/appearance.*—Six-valved, dehiscent, broad ellipsoidal capsule.

*Length*.—About 8 mm.

*Diameter*.—About 6 mm.

*Mature color*.—Close to 200C. Each capsule contains multiple seeds that are about 5 mm long, 3 mm wide, and close to 200C in color.

Disease/pest resistance: Plants of the claimed *Lagerstroemia* variety grown in field and container trials have exhibited resistance to powdery mildew and *Cercospora* leaf spot.

I claim:

1. A new and distinct *Lagerstroemia* plant named 'PIILAG-I', as illustrated and described herein.

* * * * *